(12) United States Patent
Jabri et al.

(10) Patent No.: US 8,139,710 B2
(45) Date of Patent: Mar. 20, 2012

(54) SYSTEMS, METHODS AND APPARATUS TO IMAGE OBJECTS

(75) Inventors: Kadri Nizar Jabri, Waukesha, WI (US); Gopal B. Avinash, New Berlin, WI (US); Kenny K. Israni, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 429 days.

(21) Appl. No.: 11/750,488

(22) Filed: May 18, 2007

(65) Prior Publication Data

US 2008/0285711 A1 Nov. 20, 2008

(51) Int. Cl.
*A61B 6/03* (2006.01)
(52) U.S. Cl. .......................................... 378/22
(58) Field of Classification Search ............... 378/20–22
See application file for complete search history.

(56) References Cited

U.S. PATENT DOCUMENTS

| | | | |
|---|---|---|---|
| 5,566,282 A * | 10/1996 | Zuiderveld | 345/424 |
| 6,101,236 A * | 8/2000 | Wang et al. | 378/4 |
| 6,236,708 B1 * | 5/2001 | Lin et al. | 378/22 |
| 6,529,575 B1 * | 3/2003 | Hsieh | 378/4 |
| 6,888,924 B2 * | 5/2005 | Claus et al. | 378/163 |
| 7,167,866 B2 | 1/2007 | Farnham et al. | |
| 2002/0114498 A1 | 8/2002 | Op De Beek et al. | |
| 2004/0228453 A1 * | 11/2004 | Dobbs et al. | 378/210 |
| 2005/0002550 A1 * | 1/2005 | Jabri et al. | 382/131 |
| 2005/0226482 A1 * | 10/2005 | Kuduvalli | 382/128 |
| 2006/0098855 A1 * | 5/2006 | Gkanatsios et al. | 382/128 |
| 2006/0204076 A1 | 9/2006 | Avinash et al. | |
| 2007/0036265 A1 * | 2/2007 | Jing et al. | 378/37 |
| 2008/0069419 A1 * | 3/2008 | Farag et al. | 382/131 |

FOREIGN PATENT DOCUMENTS

WO WO 2006040715 A1 * 4/2006

OTHER PUBLICATIONS

Dobbins et al., Digital x-ray tomosynthesis: current state of the art and clinical potential, Topical Review, 2003, Physics in Medicine and Biology, vol. 48, pp. R65-R106.*
Steil et al., Digital Flashing Tomosynthesis: A promising Technique for Angiocardiographic Screening, 1993, IEEE, vol. 12, No. 2, pp. 314-321.*
Bertram et al., Directional Interpolation of Sparsely Sampled Cone-Beam CT Sinogram Data, 2004, IEEE pp. 928-931.*
Weisstein, Eric W., Pivot Point, From MathWorld—A Wolfram Web Resource. http://mathworld.wolfram.com/PivotPoint.html, Downloaded from website on Oct. 21, 2010.*
David Getty, Update Course: Advances in Digital Radiography—Digital Radiographic Advanced Methods for Depth Discrimination, session code RC825, session presentation at RSNA 2004 convention, Chicago, IL, Dec. 3, 2004.
F. Lekien and J. Marsden,International Journal for Numerical Methods in Engineering, Int. J. Numer. Meth. Engng 2005; 63:455-471, Published on the Internet on Mar. 3, 2005 in Wiley InterScience (www.interscience.wiley.com). DOI: 10.1002/nme.1296.

* cited by examiner

*Primary Examiner* — Edward Glick
*Assistant Examiner* — John Corbett
(74) *Attorney, Agent, or Firm* — William Baxter, Esq.; Michael G. Smith, Esq.

(57) ABSTRACT

Systems, methods and apparatus are provided through which in some embodiments a time series is generated from a plurality of X-ray projections of an object that were acquired under limited angular conditions with a flat-panel X-ray detector, and thereafter the plurality of X-ray projections in the time series are displayed in reference to a pivot point.

15 Claims, 7 Drawing Sheets

SYSTEMS, METHODS AND APPARATUS TO IMAGE OBJECTS

FIELD OF THE INVENTION

This invention relates generally to digital imaging, and more particularly to digital medical tomosynthesis.

BACKGROUND OF THE INVENTION

Digital tomosynthesis is an imaging technique that enables three-dimensional (3D) imaging of the patient. Acquisition of tomosynthesis images is performed using a large-area digital detector that is typically used for conventional single projection radiography. 3D data is reconstructed from a number of imaged slices through the anatomy, each slice being parallel to the detector plane.

In conventional tomosynthesis, an X-ray source delivers multiple exposures during a single "sweep" from multiple projection angles. Conventional tomosynthesis acquisition consists of a number of projections of X-ray exposures covering an angular range less than 180 degrees, typically 20 to 50 degrees. The system includes only one X-ray source. The patient stands near the detector plane during the tomosynthesis scan. The number of projections for a single wallstand scan can range from about 30 to 60. The sweep angle is the angle from the first to the final projection focal spot with respect to the focal plane.

The X-ray source is moved to different focal spot positions and a projection image is acquired at each position. After tomosynthesis acquisition, the digital images acquired at the detector are reconstructed into multiple image slices, parallel to the flat panel detector face, using a computerized reconstruction algorithm. The flat panel detector provides rapid response, excellent dynamic range and digital images for input to the reconstruction software.

Viewing reconstructed slices is the customary and primary method of visualizing digital tomosynthesis imaging data. However, a common complication of the process of slice reconstruction is reconstruction artifacts. The artifacts result mainly from an insufficient number of projections, limited angle of data acquisition, and ill-posed nature of the limited view reconstruction.

Motion of a patient also causes complications in visualization of tomosynthesis data as reconstructed slices. Conventional slice reconstruction processes assume an immobile imaged object. However, an imaged patient can and often does move relative to the imaging system. Since these exams take several seconds—heart, vascular and respiratory motion is usually inevitable and will lead to motion artifacts in slices.

In certain applications, measuring the extent of motion can be very important. For example, in radiation therapy applications involving moving organs, adequately distributing radiation dosage to hit the moving target is very important. As another example, in planning a minimally invasive surgery or a surgical biopsy, a fairly accurate knowledge of the organ motion would help plan for accessing the target region.

For the reasons stated above, and for other reasons stated below which will become apparent to those skilled in the art upon reading and understanding the present specification, there is a need in the art for reducing artifacts in digital tomosynthesis 3D image. There is also a need for improved measurement of patient motion during the image acquisition.

BRIEF DESCRIPTION OF THE INVENTION

The above-mentioned shortcomings, disadvantages and problems are addressed herein, which will be understood by reading and studying the following specification.

In one aspect, a method to image objects includes generating a time series of a plurality of X-ray projections of an object acquired under limited angular conditions with a flat-panel detector in which the plurality of X-ray projections are suitable for tomosynthesis reconstruction, receiving an indicated pivot point and thereafter displaying the plurality of X-ray projections in the time series in reference to the pivot point.

In another aspect, a method to visualize tomosynthesis projection images includes accessing a plurality of X-ray projections of an object under limited angular conditions from a flat-panel detector in which the plurality of X-ray projections are suitable for tomosynthesis reconstruction, generating a time series display of the plurality of X-ray projections, receiving an indicated pivot point, and displaying the time-series display of the plurality of X-ray projections.

In yet another aspect, a system to image objects includes an X-ray source, a detector that is positioned to receive X-rays emitted from the X-ray source, a processor and software apparatus that is operative on the processor to provide a depth visualization of a reconstructed dataset from a tomosynthesis acquisition and to provide a dynamic visualization of a plurality of projection images from the tomosynthesis acquisition simultaneously with providing the slice visualization.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, embodiments of methods are described. In the third section, a hardware and the operating environment in conjunction with which embodiments may be practiced are described. In the fourth section, particular implementations are described. Finally, in the fifth section, a conclusion of the detailed description is provided.

System Level Overview

Figure 1:
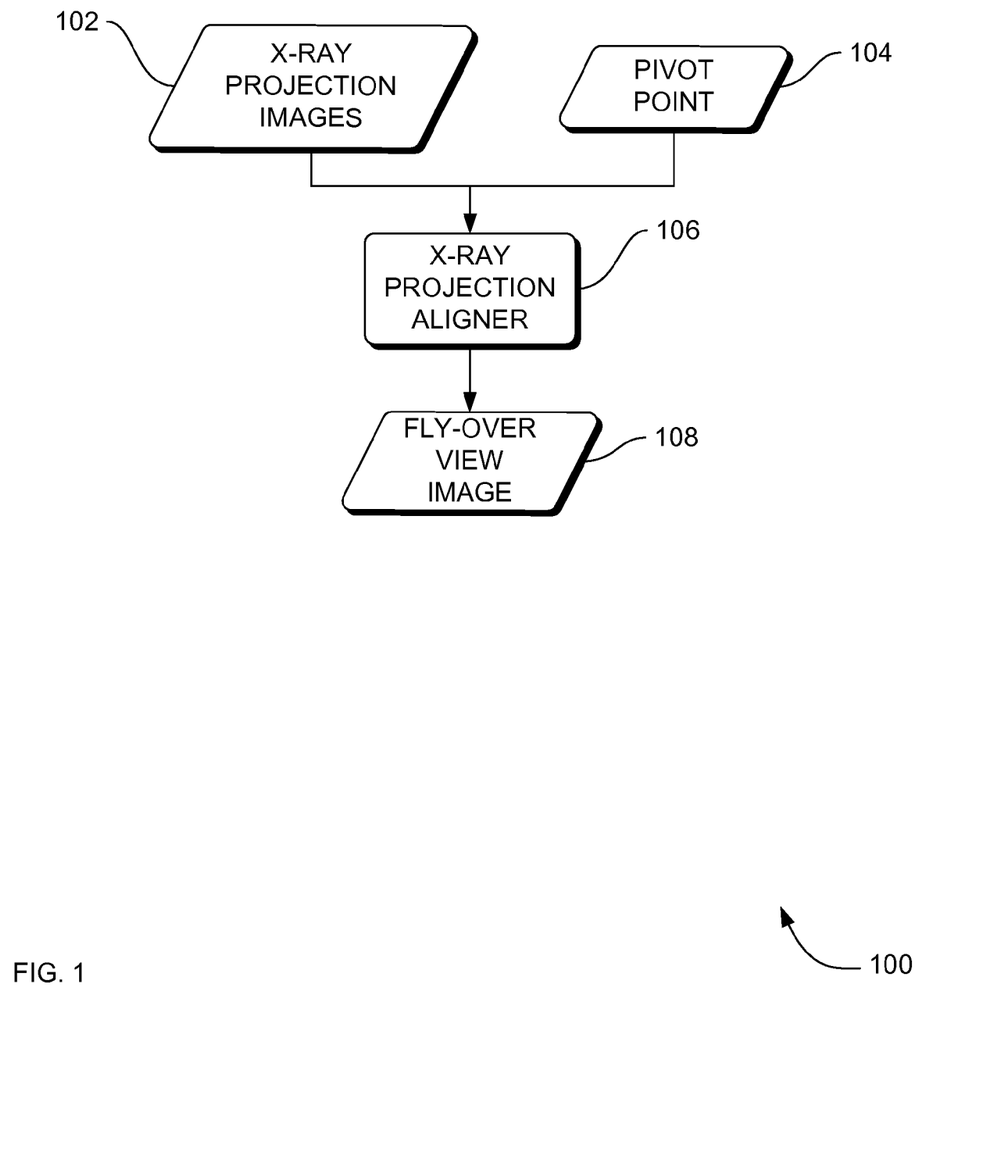
FIG. 1 is a block diagram of an overview of a system to visualize digital tomosynthesis images.

FIG. 1 is a block diagram of an overview of a system 100 to visualize digital tomosynthesis images. System 100 solves the need in the art to reduce artifacts in digital tomosynthesis three-dimensional (3D) images and solves the need in the art for improved measurement of patient motion during the image acquisition.

System 100 includes X-ray projection images 102 and a pivot point 104 that are accessed or received by an X-ray projection aligner 106. The X-ray projection aligner 106 generates a fly-over view image 108 from the X-ray projection images 102 and a pivot point 104. The fly-over view image 108 is a visual depiction of an imaged object in a linear sequential movement from one position to another, from a variety of angles. The fly-over view image 108 includes visual depiction of tomosynthesis data of three-dimensional (3D) information without reconstructing image slices across the imaged object. As a result, fewer reconstruction artifacts, such as ripple effects, are introduced into the fly-over view 108 during processing of the X-ray projection images 102.

The pivot point 104 is a point in space about which or from which the imaged object is viewed. In some examples, the pivot point 104, is thought of as a center or focus, sometimes called the origin. In some notations, the pivot point 104 is described in terms of three axes, X, Y and Z. In some embodiments the pivot 104 is defined relative to the imaged object. In some embodiments the pivot point 104 is defined in terms of absolute locations.

System 100 is tolerant of patient/anatomy motion artifacts due to the visualization being a time series display of actual projection images in which system 100 excludes the incorrect assumption that the imaged object is immobile. Image noise is screened out from the fly-over view image 108 by the human visual system while still detecting clinically relevant detail. System 100 also provides detection of clinically relevant time-varying information (e.g., the beating of the heart in chest image).

While the system 100 is not limited to any particular X-ray projection image 102, pivot point 104, X-ray projection aligner 106 and fly-over view 108, for sake of clarity, simplified X-ray projection images 102, pivot point 104, X-ray projection aligner 106 and fly-over view 108 are described.

The system level overview of the operation of an embodiment is described above in this section of the detailed description. Some embodiments operate in a multi-processing, multi-threaded operating environment on a computer.

Method Embodiments

In the previous section, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 200-500 are performed by a program executing on, or performed by firmware or hardware that is a part of, a computer.

Figure 2:
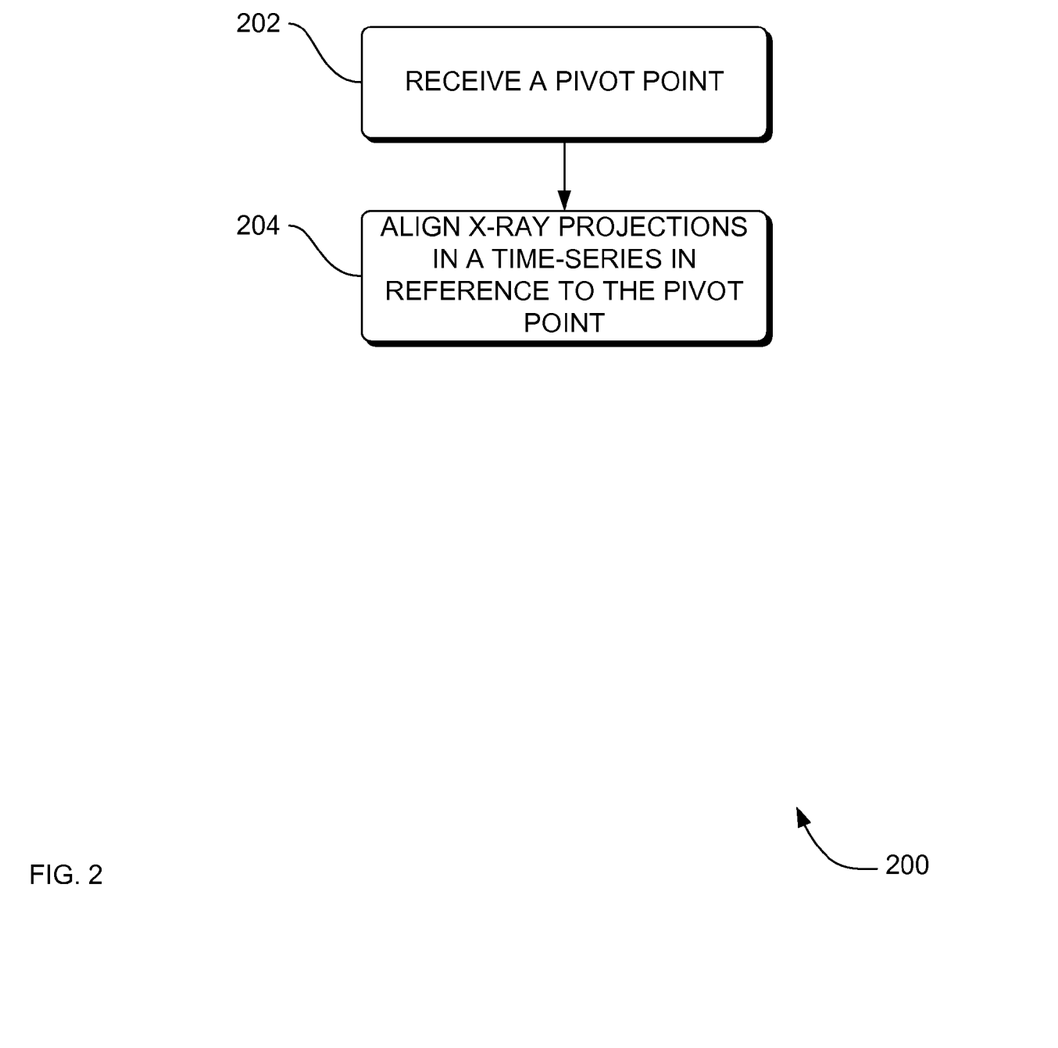
FIG. 2 is a flowchart of a method to image objects, according to an embodiment.

FIG. 2 is a flowchart of a method 200 to image objects, according to an embodiment. Method 200 includes receiving a pivot point at block 202. In some embodiments, the pivot point is received to a memory apparatus or device. In some embodiments, the pivot point is received from a user. In some embodiments, the pivot point/plane can be selected by letting the user specify the approximate height from the detector using an appropriate user interface. In another embodiment, the pivot point can be selected by first reconstructing and presenting to the user conventional slices and then allowing the user to point/click on a single point in a single slice and designate it as the pivot point. In yet other embodiments, the pivot point is generated by an automated means (algorithm, segmentation, CAD, etc.).

Method 200 also includes aligning X-ray projections in a time-series in reference to the pivot point, at block 204. In some embodiments, the aligning at block 204 is performed by the X-ray projection aligner 106 in FIG. 1 above, generating the fly-over view image 108.

Figure 3:
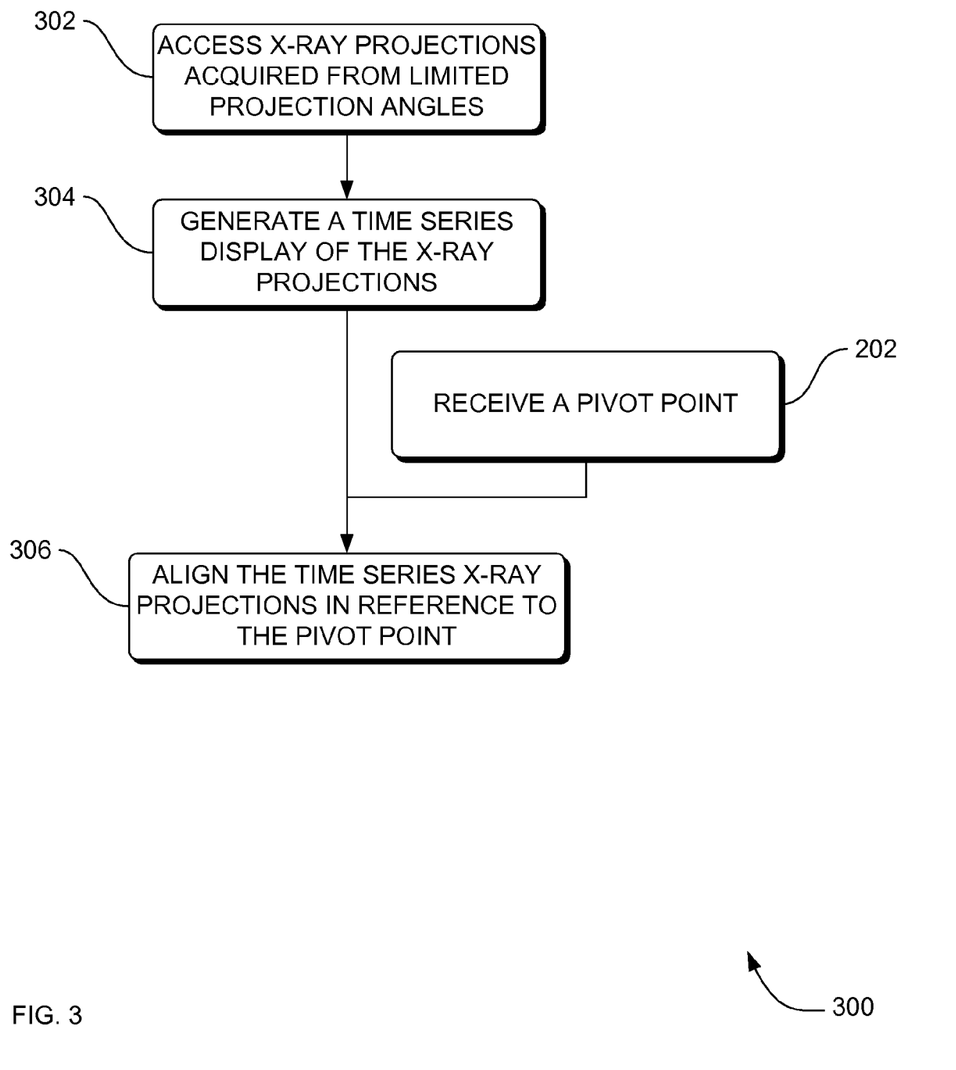
FIG. 3 is a flowchart of a method to image an object, according to an embodiment.

FIG. 3 is a flowchart of a method 300 to image an object, according to an embodiment. Some embodiments of method 300 include accessing a plurality of X-ray projections of an object under limited angular conditions from a flat-panel detector, at block 302. The plurality of X-ray projections are suitable for tomosynthesis reconstruction.

Method 300 also includes generating a time series display of the plurality of X-ray projections in some embodiments, at block 304. In some embodiments, the time series display is generated to a memory device or apparatus. Method 300 also includes in some embodiments receiving a pivot point, at block 202, or in other embodiments, the pivot point is received from another source. For example, the pivot point can be determined or calculated from an approximate distance from the detector that is specified by a user or derived from a user editable configuration file.

At block 306, method 300 includes in some embodiments aligning one or more processed projection images in reference to the pivot point, to simulate a fly-over view image 108 of the imaged object. In some embodiments, the processed projection image(s) are aligned based on or in reference to the geometry of the imaged object.

Figure 4:
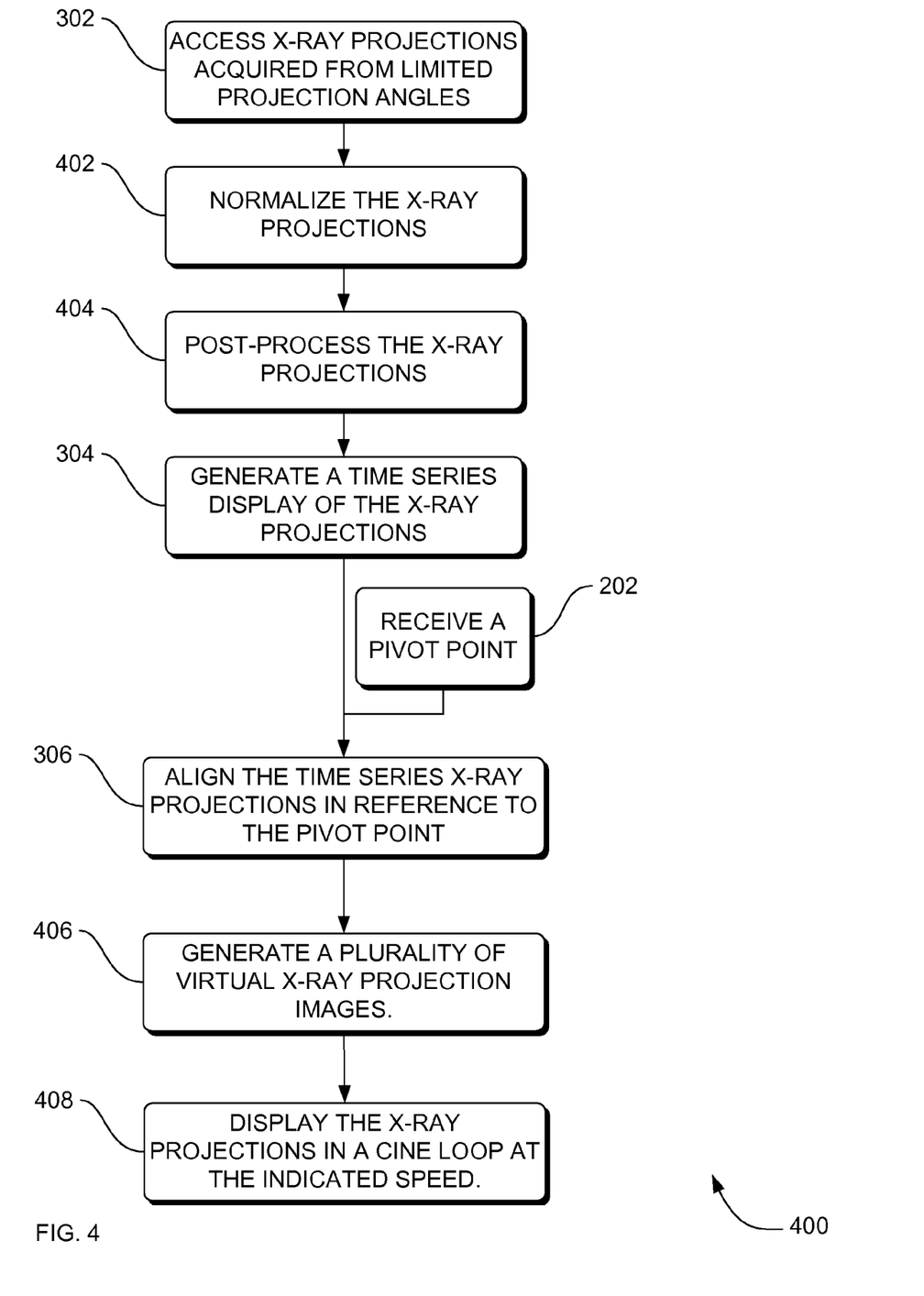
FIG. 4 is a flowchart of a method to visualize tomosynthesis projection images, according to an embodiment.

FIG. 4 is a flowchart of a method 400 to visualize tomosynthesis projection images, according to an embodiment. Some embodiments of method 400 include accessing a plurality of X-ray projections of an object under limited angular conditions from a flat-panel detector, at block 302. Some embodiments of method 400 also include normalizing the X-ray projections, at block 402. In some embodiments, normalizing the X-ray projections, involves transforming the intensity map to the standard range of intensity values, i.e., $\{0, 1, \ldots, 16383\}$.

Method 400 also includes in some embodiments post-processing the X-ray projections, at block 404. Post-processing includes processes such as edge enhancement, spatial noise reduction, frequency-based noise reduction, signal-dependent noise reduction, contrast enhancement, dynamic range compression, histogram equalization, shuttering of unexposed image regions, and presentation processing such as automatic display window level (brightness) and window width (contrast) adjustments for optimal display.

Some embodiment of method 400 also include generating a time series display of the plurality of X-ray projections in some embodiments at block 304, receiving a pivot point at block 202, and/or aligning one or more processed projection images in reference to the pivot point, to simulate a fly-over view image 108 of the imaged object.

Some embodiments of method 400 also include generating a plurality of virtual projection images, at block 406, and displaying the time series display of the plurality of X-ray projections using the pivot point, at block 408. In some embodiments, the virtual projection images are interpolated projection images, distinguished from acquired projection images. The interpolated projection images may be helpful in avoiding jerkiness in the visualization. The interpolation can be performed using trilinear or tricubic methods. Trilinear interpolation is a method of multivariate interpolation on a 3-dimensional tensor product grid (possibly with an arbitrary, non-overlapping grid points in each dimension, but i.e. not an arbitrarily triangularized finite element mesh) of discretely sampled data. The results of trilinear interpolation approximate the value of an intermediate point (x,y,z) within the local axial rectangular prism linearly, using data on the lattice points.

Figure 5:
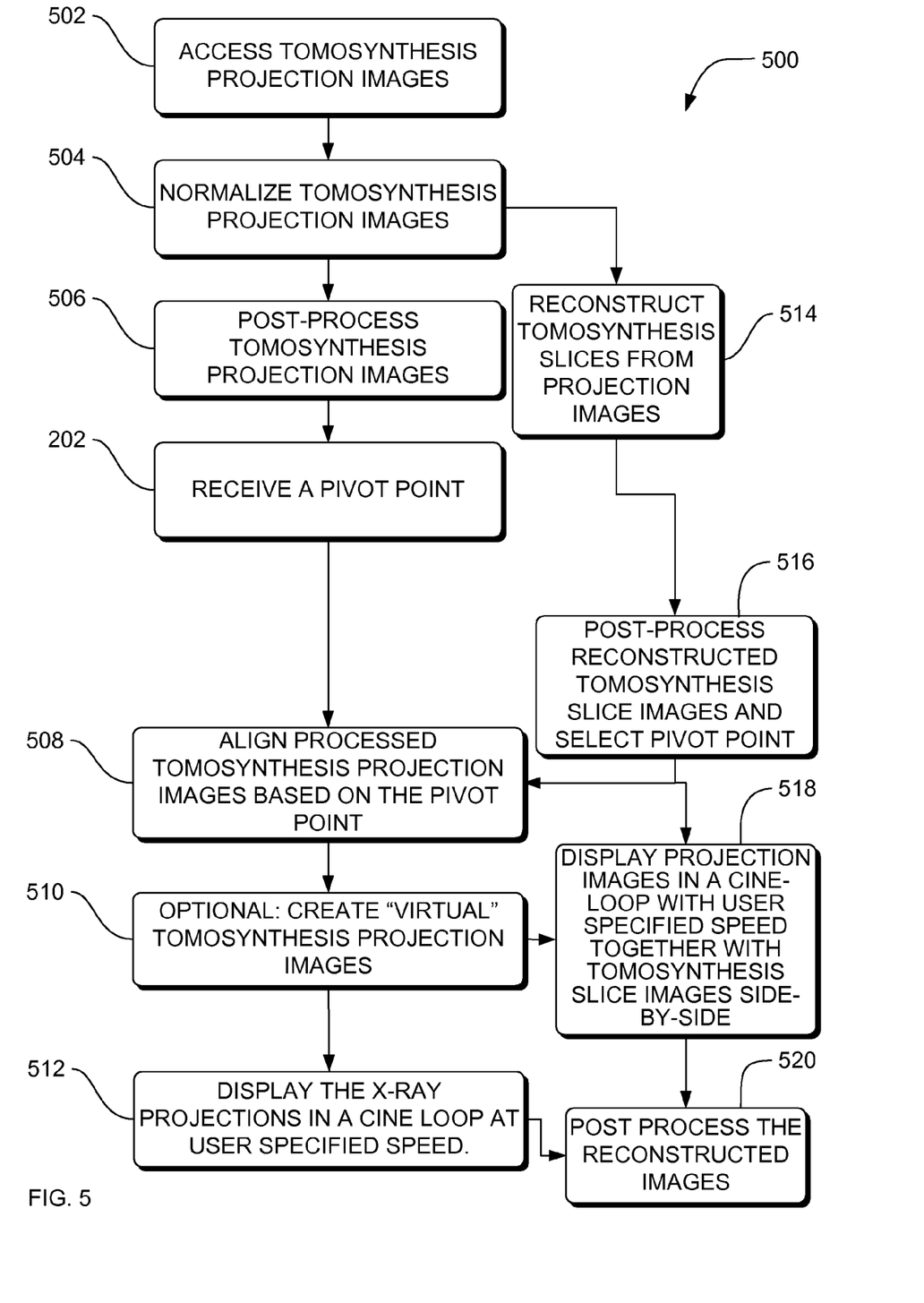
FIG. 5 is a flowchart of a method to visualize tomosynthesis projection images, according to an embodiment.

FIG. 5 is a flowchart of a method 500 to visualize tomosynthesis projection images, according to an embodiment. Some embodiments of method 500 include accessing a plurality of X-ray projections at block 502. In some instances, the X-ray projections of the imaged object were acquired under limited angular conditions from a flat-panel detector. In some instances, the plurality of X-ray projections are suitable for tomosynthesis reconstruction.

Method 500 also includes in some embodiments generating a time series display of the plurality of tomosynthesis X-ray projections, at block 504. In some embodiments, the time series display is generated to a memory device or apparatus.

Thereafter, the processing of method 500 can include multiple branches of paths of execution. For example, in some embodiments, method 500 includes post-processing the X-ray projections, at block 506, receiving an indicated pivot point, at block 202, and aligning the post-processed tomosynthesis X-ray projections in a time-series in reference to the pivot point, at block 508. In some embodiments, the aligning at block 508 is performed by the X-ray projection aligner 106 in FIG. 1 above, generating the fly-over view image 108.

Some embodiments of method 500 also include generating a plurality of tomosynthesis virtual projection images, at block 510, and displaying the time series display of the plurality of tomosynthesis X-ray projections using the pivot point, at a speed that is specified by the user, at block 512.

In some embodiments of method 500, one or more slices are reconstructed at block 514 from the tomosynthesis X-ray projections that were accessed at block 502, the reconstructed tomosynthesis slice(s) are post-processed and a pivot point is selected at block 516, and the reconstructed slice(s) are displayed to a user, at block 512.

Method 500 also includes in some embodiments, displaying projection images in a cine-loop with user specified speed together with tomosynthesis slice images side-by-side, at block 518.

Method 500 also includes in some embodiments, post-processing the reconstructed images, at block 520.

In some embodiments, methods 200-500 are implemented as a computer data signal embodied in a carrier wave, that represents a sequence of instructions which, when executed by a processor, such as a processor, cause the processor to perform the respective method. In other embodiments, methods 200-500 are implemented as a computer-accessible medium having executable instructions capable of directing a processor to perform the respective method. In varying embodiments, the medium is a magnetic medium, an electronic medium, or an optical medium.

The following description provides an overview of computer hardware and a suitable computing environment in conjunction with which some embodiments can be implemented. Embodiments are described in terms of a computer executing computer-executable instructions. However, some embodiments can be implemented entirely in computer hardware in which a computer-executable instructions are implemented in read-only memory. Some embodiments can also be implemented in client/server computing environments where remote devices that perform tasks are linked through a communications network. Program modules can be located in both local and remote memory storage devices in a distributed computing environment.

A computer includes a processor, commercially available from Intel, Motorola, Cyrix and others. A computer also includes random-access memory (RAM), read-only memory (ROM), one or more mass storage devices, and a system bus, that operatively couples various system components to the processing unit. The memory and mass storage devices are types of computer-accessible media. Mass storage devices are more specifically types of nonvolatile computer-accessible media and can include one or more hard disk drives, floppy disk drives, optical disk drives, and tape cartridge drives. The processor executes computer programs stored on a computer-accessible media.

A computer can be communicatively connected to the Internet via a communication device. Internet connectivity is well known within the art. In one embodiment, a communication device is a modem that responds to communication drivers to connect to the Internet via what is known in the art as a "dial-up connection." In another embodiment, a communication device is an Ethernet® or similar hardware network card connected to a local-area network (LAN) that itself is connected to the Internet via what is known in the art as a "direct connection" (e.g., T1 line, etc.).

A user enters commands and information into a computer through input devices such as a keyboard or a pointing device. The keyboard permits entry of textual information into computer, as known within the art, and embodiments are not limited to any particular type of keyboard. Pointing device permits the control of the screen pointer provided by a graphical user interface (GUI) of operating systems such as versions of Microsoft Windows®. Embodiments are not limited to any particular pointing device. Such pointing devices include mice, touch pads, trackballs, remote controls and point sticks. Other input devices (not shown) can include a microphone, joystick, game pad, satellite dish, scanner, or the like.

In some embodiments, a computer is operatively coupled to a display device. The display device is connected to the system bus. Display device permits the display of information, including computer, video and other information, for viewing by a user of a computer. Embodiments are not limited to any particular display device. Such display devices include cathode ray tube (CRT) displays (monitors), as well as flat panel displays such as liquid crystal displays (LCD's). In addition to a monitor, computers typically include other peripheral input/output devices such as printers (not shown). Speakers and provide audio output of signals. The speakers are also connected to the system bus.

A computer also includes an operating system (not shown) that is stored on a computer-accessible media, the RAM, the ROM, and/or the mass storage device, and is executed by the processor. Examples of operating systems include Microsoft Windows®, Apple MacOS®, Linux®, UNIX®. Examples are not limited to any particular operating system, however, and the construction and use of such operating systems are well known within the art.

Embodiments of a computer are not limited to any type of computer. In varying embodiments, a computer comprises a PC-compatible computer, a MacOS®-compatible computer, a Linux®-compatible computer, or a UNIX®-compatible computer. The construction and operation of such computers are well known within the art.

A computer can be operated using at least one operating system to provide a graphical user interface (GUI) including a user-controllable pointer. A computer can have at least one web browser application program executing within at least one operating system, to permit users of a computer to access an intranet, extranet or Internet world-wide-web pages as addressed by Universal Resource Locator (URL) addresses. Examples of browser application programs include Netscape Navigator® and Microsoft Internet Explorer®.

A computer can operate in a networked environment using logical connections to one or more remote computers. These logical connections are achieved by a communication device coupled to, or a part of, a computer. Embodiments are not limited to a particular type of communications device. The remote computer can be another computer, a server, a router, a network PC, a client, a peer device or other common network node. The logical connections include a local-area network (LAN) and a wide-area network (WAN). Such networking environments are commonplace in offices, enterprise-wide computer networks, intranets, extranets and the Internet.

When used in a LAN-networking environment, a computer and remote computer are connected to the local network through network interfaces or adapters, which is one type of communications device. Remote computer also includes a network device. When used in a conventional WAN-networking environment, a computer and remote computer communicate with a WAN through modems (not shown). The modem, which can be internal or external, is connected to the system bus. In a networked environment, program modules depicted relative to a computer, or portions thereof, can be stored in the remote computer.

A computer also includes at least one power supply. Each power supply can be a battery.

Methods 200-500 can be embodied as computer hardware circuitry or as a computer-readable program, or a combination of both. In another embodiment, methods 200-500 are implemented in an application service provider (ASP) system.

More specifically, in a computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer, or on at least as many computers as there are components.

Apparatus

Figure 6:
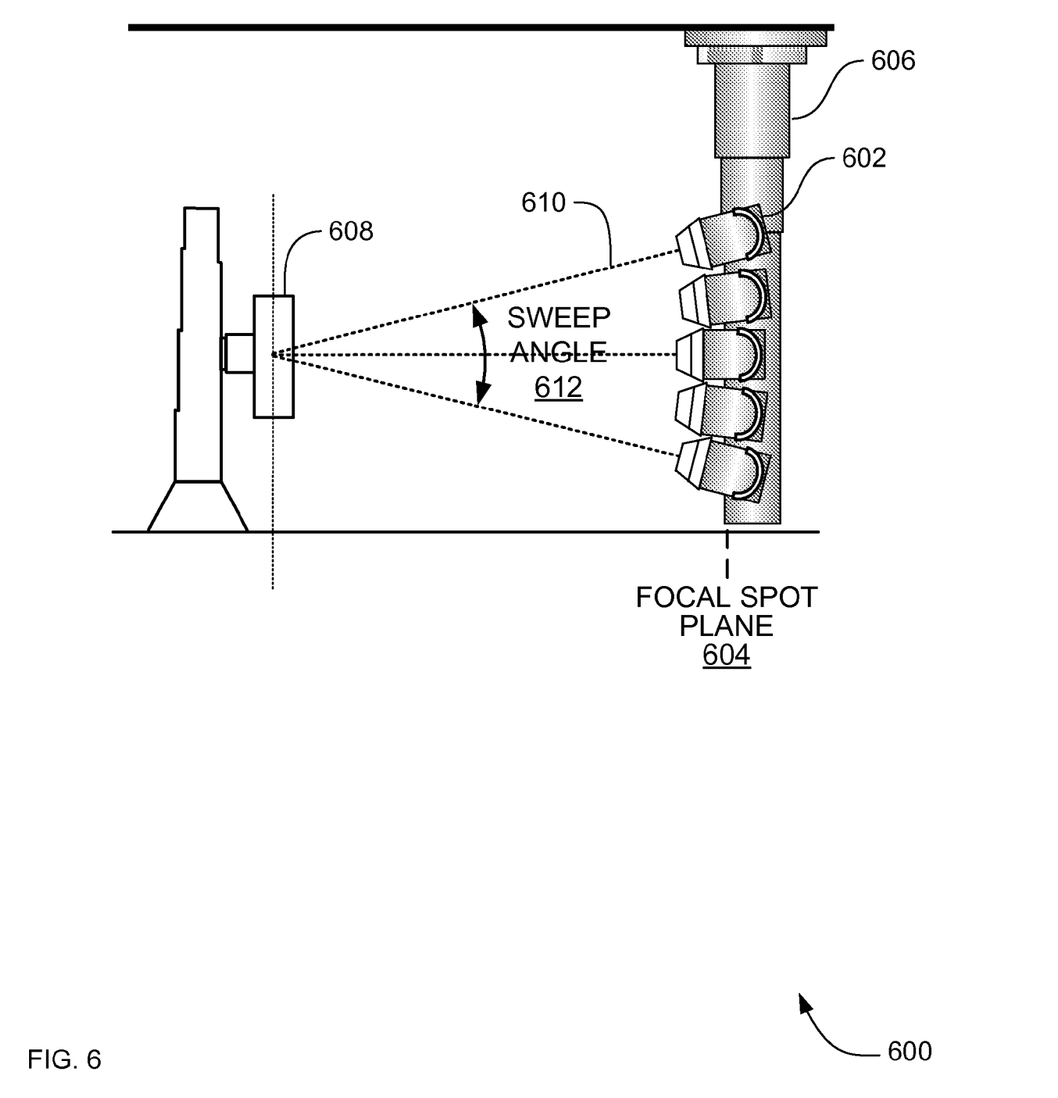
FIG. 6 is a block diagram of an apparatus to perform tomosynthesis image acquisition in a wall-stand configuration.
Figure 7:
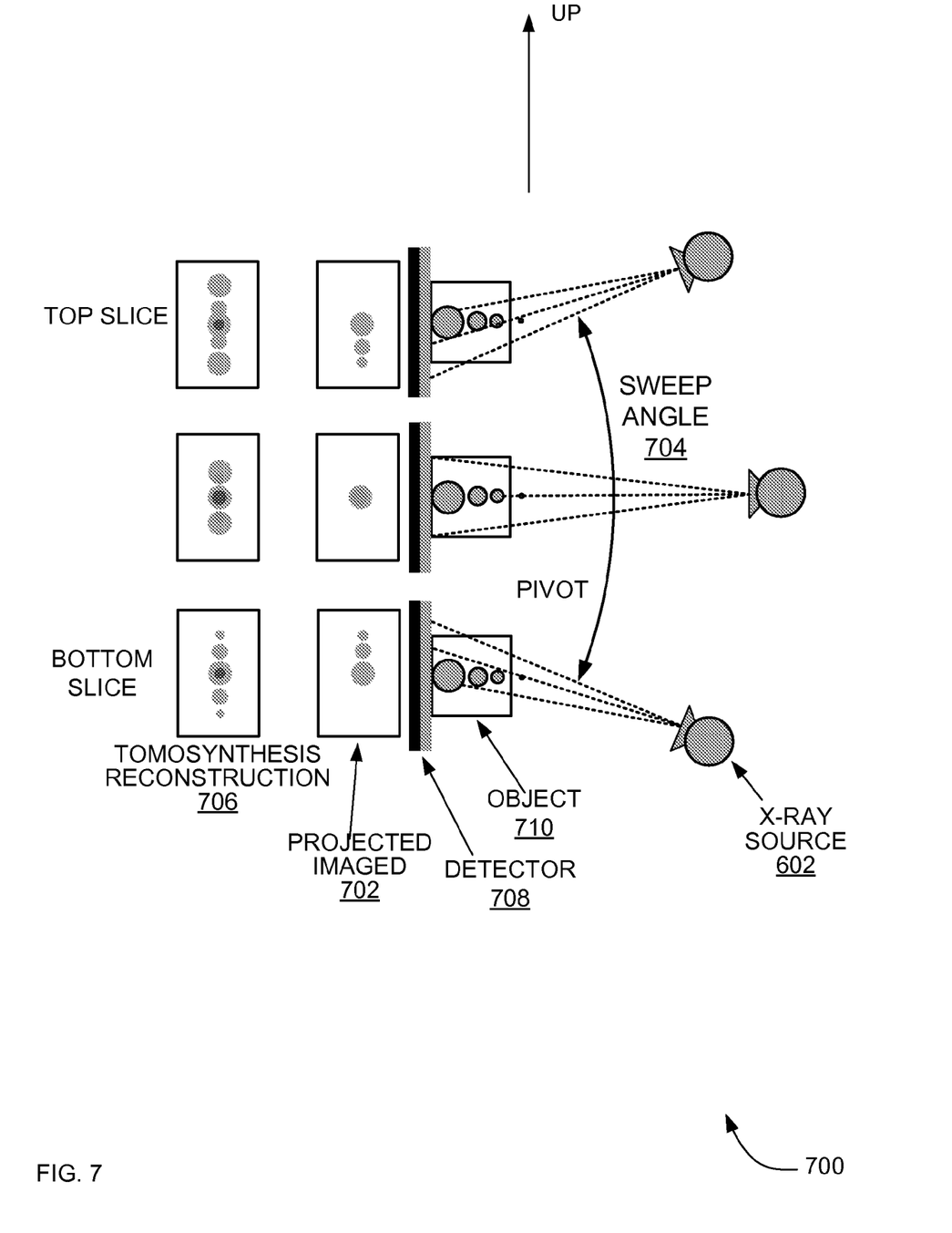
FIG. 7 is a block diagram of a digital radiographic tomosynthesis acquisition system.

Referring to FIGS. 6-7, particular implementations is described in conjunction with the system overview in FIG. 1 and the methods described in conjunction with methods 200-700.

FIG. 6 is a block diagram of an apparatus 600 to perform tomosynthesis image acquisition in a wall-stand configuration. In FIG. 6, an X-ray source 602 is transported along a focal spot plane, such as vertical focal spot plane 604. In some embodiments, the X-ray source 602 is transported along the focal spot plane by an overhead tube suspension system (OTS).

As the X-ray source 602 is transported along the focal spot plane, the X-ray source is rotated along an axis transverse to the focal spot plane in order to focus on a fixed target destination position of the flat-panel digital X-ray detector 608. The X-ray beam 610 maintains directional focus on the flat-panel digital X-ray detector 608 at all times during imaging while the X-ray source 602 is transported along the focal spot plane. The distance of movement of the X-ray source 602 along the focal spot plane defines the sweep angle 612 of the imaging. The sweep angle 612 defines the limited angular conditions of the image acquisition. The sweep angle 612 is helpful, if not in some instances, necessary to provide a depth visualization of a reconstructed dataset from a tomosynthesis acquisition and provide a dynamic visualization of a plurality of projection images from the tomosynthesis acquisition.

FIG. 7 is a block diagram of a digital radiographic tomosynthesis acquisition system 700. In FIG. 7, a sequence of discrete projection images 702 is acquired over a limited angular range 704, which provides the retrospective reconstruction of tomographic slices 706 that are parallel to a detector plane 708 through an imaged object 710.

CONCLUSION

Visual tomosynthesis image projection is described. A technical effect of the visual tomosynthesis image projection is a fly-over image view of an imaged object. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application is meant to include all object-oriented, digital X-ray imaging, and communication environments and alternate technologies which provide the same functionality as described herein.

We claim:

1. A method to image objects, the method comprising:
    generating to a memory, a time series of a plurality of X-ray projections of an object acquired under limited angular conditions with a flat-panel detector, wherein the plurality of X-ray projections are suitable for tomosynthesis reconstruction;
    generating a plurality of virtual X-ray projection images, wherein the virtual projection images are interpolated projection images, generated from a trilinear method using multivariate interpolation on a 3-dimensional tensor product grid with arbitrary and non-overlapping grid points in each of a plurality of dimensions, which approximates the value of an intermediate 3-dimensional point within the local axial rectangular prism linearly from data on lattice points; and displaying the plurality of virtual X-ray projection images in the time series.

2. The method of claim 1 further comprising:
reconstructing at least one slice from the projections; and
displaying the reconstructed slice.

3. The method of claim 1 further comprising:
performing noise reduction in the plurality of X-ray projections.

4. The method of claim 1 further comprising:
presentation processing.

5. The method of claim 1 further comprising:
reconstructing at least one slice from the projections; and
displaying the reconstructed slice.

6. The method of claim 1 further comprising:
providing a depth visualization of a reconstructed dataset from a tomosynthesis acquisition; and
providing a dynamic visualization of a plurality of projection images from the tomosynthesis acquisition, simultaneously with providing the slice visualization.

7. The method of claim 1 further comprising:
receiving an indicated display speed; and
displaying the projections in a cine loop at the indicated speed.

8. A non-transitory computer-accessible medium having executable instructions to image objects, the executable instructions capable of directing a processor to perform:
accessing a plurality of X-ray projections of an object under limited angular conditions from a flat-panel detector, wherein the plurality of X-ray projections are suitable for tomosynthesis reconstruction;
generating to a memory, a time series display of the plurality of X-ray projections;
generating a plurality of virtual projection images, wherein the virtual projection images are interpolated projection images, generated from a trilinear method using multivariate interpolation on a 3-dimensional tensor product grid with arbitrary and non-overlapping grid points in each of a plurality of dimensions, which approximates the value of an intermediate 3-dimensional point within the local axial rectangular prism linearly from data on lattice points; and
displaying the time-series display of the plurality of virtual X-ray projection images.

9. The non-transitory computer-accessible medium of claim 8, the medium further comprising executable instructions capable of directing the processor to perform:
performing noise reduction in the plurality of X-ray projections.

10. The non-transitory computer-accessible medium of claim 8, the medium further comprising executable instructions capable of directing the processor to perform:
presentation processing.

11. The non-transitory computer-accessible medium of claim 8, the medium further comprising executable instructions capable of directing the processor to perform:
generating a plurality of virtual projection images.

12. A system to image objects, the system comprising:
an X-ray source;
a detector positioned to receive X-rays emitted from the X-ray source;
a processor configured to the steps of:
providing a depth visualization of a reconstructed dataset from a tomosynthesis acquisition; and
generating a plurality of virtual projection images, wherein the virtual projection images are interpolated projection images, generated from a trilinear method using multivariate interpolation on a 3-dimensional tensor product grid with arbitrary and non-overlapping grid points in each of a plurality of dimensions, which approximates the value of an intermediate 3-dimensional point within the local axial rectangular prism linearly from data on lattice points.

13. The system of claim 12, wherein the processor is further operable to:
receive an indicated display speed; and
display the projections in a cine loop at the indicated speed.

14. The system of claim 12, wherein the processor is further operable to:
access a plurality of X-ray projections of an object under limited angular conditions from a flat-panel detector, wherein the plurality of X-ray projections are suitable for tomosynthesis reconstruction;
generate to a memory, a time series display of the plurality of X-ray projections; and
display the time series display of the plurality of X-ray projections.

15. The system of claim 12, wherein the processor is further operable to:
generate a plurality of virtual projection images.

* * * * *